US006905656B1

(12) United States Patent
Ladlow et al.

(10) Patent No.: US 6,905,656 B1
(45) Date of Patent: Jun. 14, 2005

(54) PARALLEL REACTION STATION WITH MAGNETIC STIRRING

(75) Inventors: Mark Ladlow, Cambridge (GB); Adrian Walter Mitchell, Hertfordshire (GB)

(73) Assignee: Radleys Discovery Technologies Limited (GB)

( * ) Notice: Subject to any disclaimer, the term of this patent is extended or adjusted under 35 U.S.C. 154(b) by 0 days.

(21) Appl. No.: 09/509,147

(22) PCT Filed: Sep. 17, 1998

(86) PCT No.: PCT/EP98/05901

§ 371 (c)(1),
(2), (4) Date: May 25, 2000

(87) PCT Pub. No.: WO99/13988

PCT Pub. Date: Mar. 25, 1999

(30) Foreign Application Priority Data

Sep. 18, 1997 (GB) .............................................. 9719774

(51) Int. Cl.$^7$ ............................. B01L 3/00; B01L 11/00; G01N 21/00; B01F 13/08
(52) U.S. Cl. .......................... 422/99; 422/101; 422/64; 366/273; 366/274
(58) Field of Search .......................... 422/99, 101, 102, 422/104, 64–65; 366/273, 274

(56) References Cited

U.S. PATENT DOCUMENTS

| | | | | |
|---|---|---|---|---|
| 359,129 A | * | 3/1887 | Jones | 15/145 |
| 3,356,346 A | * | 12/1967 | Landsberger | 366/274 |
| 4,080,663 A | * | 3/1978 | Wik | 366/274 |
| 4,287,155 A | * | 9/1981 | Tersteeg et al. | 141/130 |
| 4,311,394 A | * | 1/1982 | Manabe | 356/39 |
| 4,345,843 A | * | 8/1982 | Berglund et al. | 366/219 |
| 4,477,192 A | | 10/1984 | Bonney | 366/274 |
| 4,568,192 A | * | 2/1986 | Kudermann et al. | 366/146 |
| 4,925,629 A | | 5/1990 | Schramm | 422/82.05 |
| 4,943,164 A | * | 7/1990 | Ohishi et al. | 366/149 |
| 5,206,479 A | * | 4/1993 | Zakaria et al. | 219/10.55 F |
| 5,272,092 A | * | 12/1993 | Hamasaki et al. | 436/172 |
| 5,409,312 A | * | 4/1995 | Fletcher | 366/208 |
| 5,499,872 A | * | 3/1996 | Baxter | 366/213 |
| 5,529,391 A | * | 6/1996 | Kindman et al. | 366/145 |
| 5,533,800 A | * | 7/1996 | Stiegelmann et al. | 366/142 |
| 5,558,839 A | * | 9/1996 | Matte et al. | 422/101 |
| 5,586,823 A | * | 12/1996 | Carr | 366/274 |

FOREIGN PATENT DOCUMENTS

| | | |
|---|---|---|
| DE | 19511588 | 3/1995 |
| WO | WO97/09353 | 3/1997 |
| WO | WO98/06485 | 2/1998 |

* cited by examiner

*Primary Examiner*—Jill Warden
*Assistant Examiner*—Brian R Gordon
(74) *Attorney, Agent, or Firm*—Foley & Lardner LLP

(57) ABSTRACT

A reaction station for performing parallel synthesis with magnetic stirring. The device is capable of accommodating a plurality of reaction vessels being specifically adapted so that when placed in a magnetic field, such as that generated by a laboratory magnetic stirrer, any reaction vessel accommodated by the device is in an effective position for stirring with respect to the magnetic field.

19 Claims, 4 Drawing Sheets

# PARALLEL REACTION STATION WITH MAGNETIC STIRRING

BACKGROUND OF THE INVENTION

The present invention relates to a device capable of accommodating a plurality of reaction vessels being specifically adapted so that when placed in a magnetic field, such as that generated by a laboratory magnetic stirrer, any reaction vessel accommodated by the device is in an effective position for stirring with respect to the magnetic field.

In the field of organic chemistry it is often desirable to perform a variety of related chemical reactions simultaneously under similar reacting conditions. The technique for performing such reactions simultaneously is known as parallel synthesis.

One of the problems associated with carrying out parallel syntheses in the laboratory is that the majority of existing laboratory magnetic stirrers are only designed to accommodate and efficiently stir the contents of one reaction vessel at any one time. Accordingly, such equipment is not suitable for use In parallel synthesis.

Laboratory magnetic stirrers specifically designed for use in parallel synthesis are known. However, such apparatus, conventionally known as parallel reaction stations are only available as complete units incorporating a source of magnetic flux together with a frame for accommodating reaction vessels. These units are very costly in comparison to laboratory magnetic stirrers. The present device is advantageous over known devices in that it allows a conventional magnetic stirrer to be used for parallel synthesis and hence provides significant economic advantages compared with parallel reaction stations.

BRIEF SUMMARY OF THE INVENTION

A means has now been found which permits the use of existing laboratory magnetic stirrers in parallel syntheses by providing a device which is capable of securely accommodating a plurality of reaction vessels said device being specifically adapted so that when correctly located within a magnetic field generated by a laboratory magnetic stirrer each and every reaction vessel is effectively positioned for stirring with respect to the magnetic field. Thereby, any reaction vessel, placed in the device and equipped with a magnetic stir bar, is subject to smooth and efficient agitation.

Thus, the present invention provides a device comprising an adapter block, the adapter block containing fixing means for holding a plurality of reaction vessels, wherein when the adapter block is co-operatively positioned within a magnetic field generated by a laboratory magnetic stirrer each and every position for holding a reaction vessel is effectively located for stirring with respect to the magnetic field. Preferably, the fixing means will comprise a plurality of sockets each designed to securely accommodate a reaction vessel.

Optionally the device may incorporate guide means which engage with the laboratory magnetic stirrer thereby ensuring the adapter block is correctly located within the magnetic field of the laboratory magnetic stirrer such that each and every position for holding a reaction vessel is effectively located for stirring with respect to the magnetic field. Suitably the guide means will ensure the adapter block is effectively positioned such that each and every position for holding a reaction vessel is effectively located for equivalent stirring with respect to the magnetic field. Preferably, the guide means comprises a raised rim around a central recess.

The adapter block may be cast in any suitable form, however in a particularly preferred arrangement the adapter block is circular in shape. The adapter block may be used in co-operation with any laboratory magnetic stirrer with a suitable circular magnetic/hotplate. Preferred laboratory stirrers include the IKA RCT basic hotplate stirrers, the IKA-MAG REO, the Heidolph MR3001, the Heidolph MR3002, and the Heidolph MR3000.

The sockets for securely accommodating the reaction vessels may be located at any position on the device in which they are effectively positioned for stirring with respect to the magnetic field. In a particularly preferred arrangement the sockets are arranged about the perimeter of the adapter block.

Preferably the adapter block is made of chemically resistant material for example PTFE or a metal such as aluminum or stainless steel.

The adapter block may optionally be constructed from heat conducting material for example aluminum or stainless steel. Thereby, when the device is used in co-operation with a hotplate/magnetic stirrer heat generated by the hotplate will be efficiently transferred to the reaction vessels accommodated by the device.

Preferably the adapter block or condenser unit will incorporate a gas manifold. Thereby, gas flow or vacuum supply to each of the reaction vessels may be individually controlled. The gas manifold may be located anywhere on the device, however in a particularly preferred arrangement the gas manifold is located at the centre of the parallel reaction station.

The adapter block is capable of being constructed to accommodate any size laboratory reaction vessel however 16 and 24 mm o.d. test tubes are particularly preferred.

Optionally the device may incorporate a condenser unit such that the contents of the reaction vessels may be heated to reflux. Suitably, the condenser unit will be assembled such that the unit is in direct contact with the reaction vessels as they project from the adapter block. Preferably the condenser unit will be constructed from a material of high specific heat capacity for example stainless steel. In a particularly preferred embodiment the unit is condenser liquid cooled.

BRIEF DESCRIPTION OF THE SEVERAL VIEWS OF THE DRAWINGS

Preferred embodiments of the invention are described in detail below, by example only, with reference to the accompanying drawings, wherein.

DETAILED DESCRIPTION OF THE INVENTION

Figure 1:
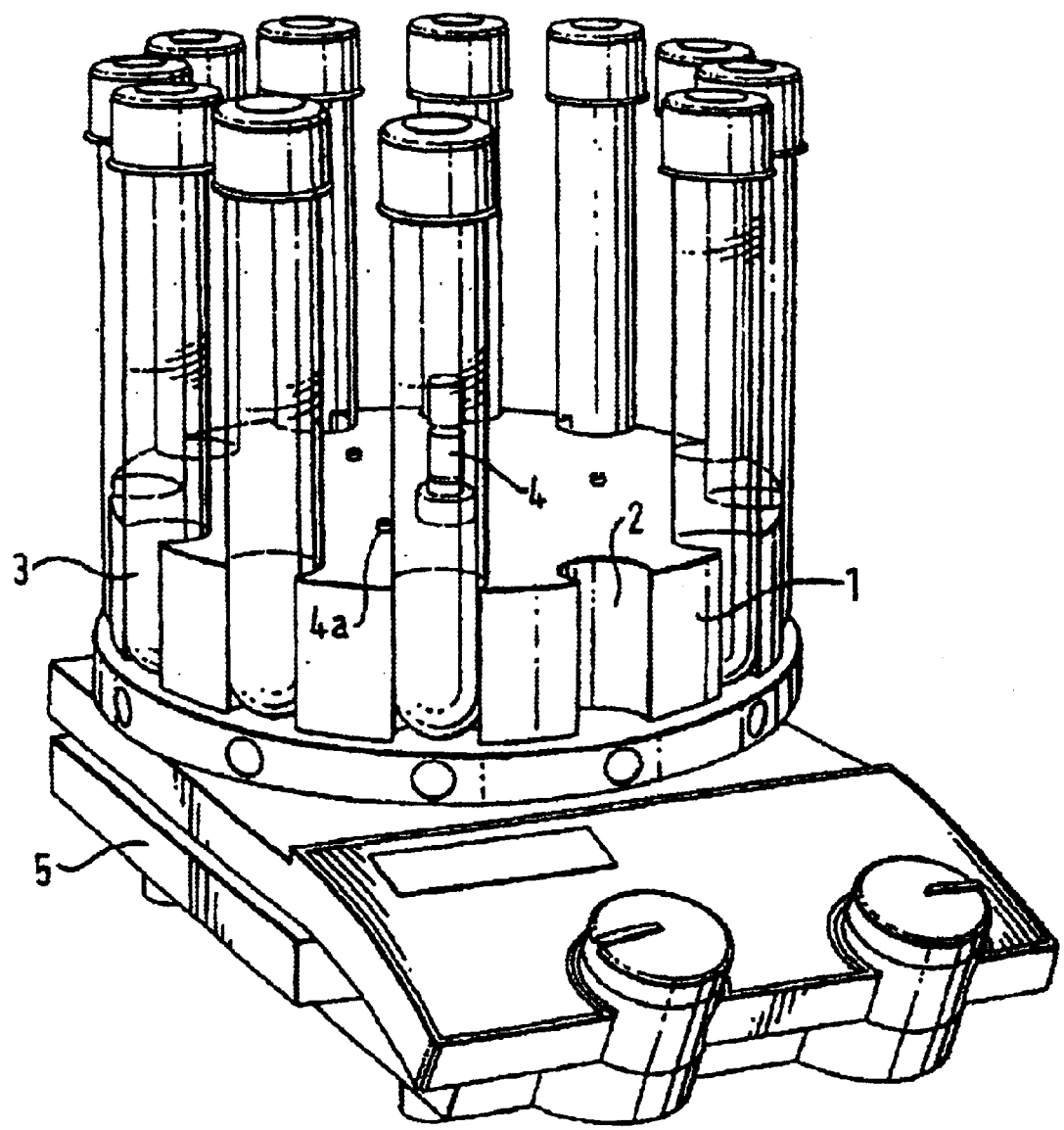
FIG. 1 is a perspective view of the adapter block working in co-operation with a laboratory magnetic stirrer.

The device illustrated in FIG. 1 comprises the adapter block (1) which is constructed from PTFE and is circular in shape with sockets (2) suitable for securely accommodating the test tube reaction vessels (3) located about the perimeter of the device. One face of the device is equipped with a central recess whereby the stirrer plate of the magnetic stirrer (5) is secured within the recess thereby ensuring that the device is effectively located for stirring within the magnetic field. A gas manifold comprising a gas inlet (4) and gas outlets (4a) is located at the centre of the adapter block.

Figure 2:
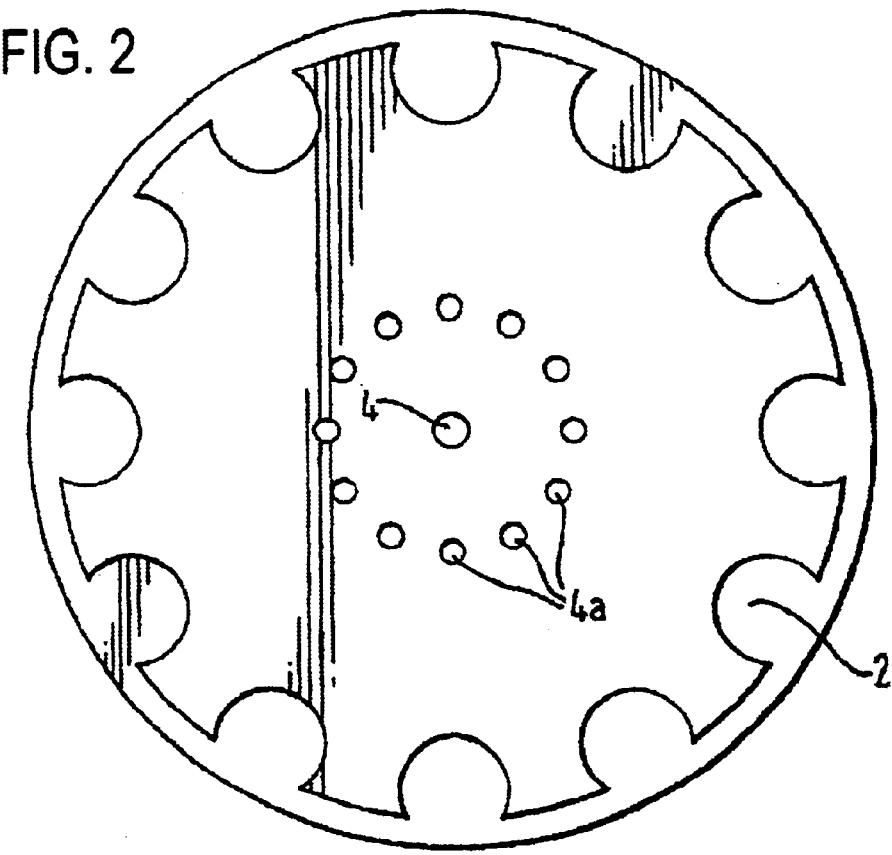
FIG. 2 is a plan view of the adapter block.
Figure 3:
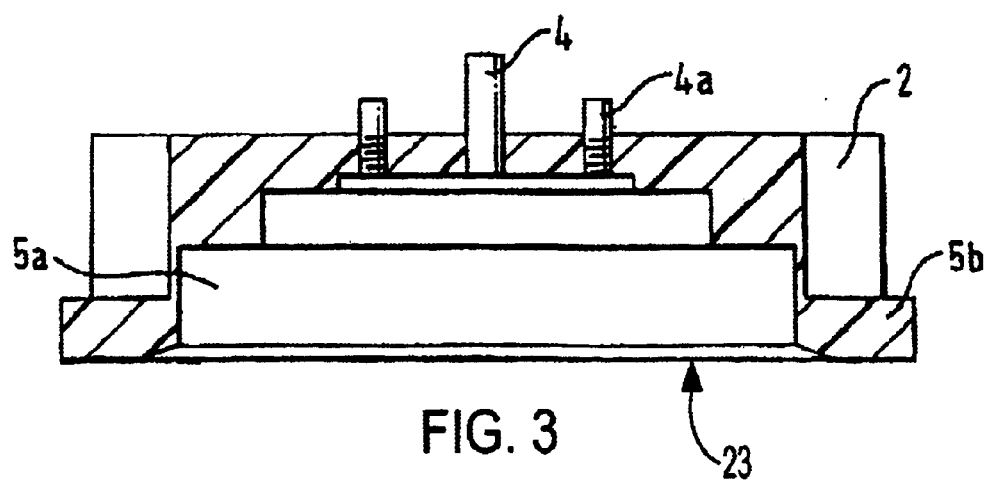
FIG. 3 is a cross-section of the adapter block.

FIGS. 2 and 3 show the location of the gas inlet (4) and gas outlets (4a) more clearly. FIG. 3 illustrates guide means, shown generally at 23, comprising the central recess (5a) formed by the raised rim (5b) in the base of the adapter block (1) below the sockets (2) for accommodating the reaction vessels (3), which ensure the adapter block is correctly located within the magnetic field of the laboratory stirrer.

Figure 4:
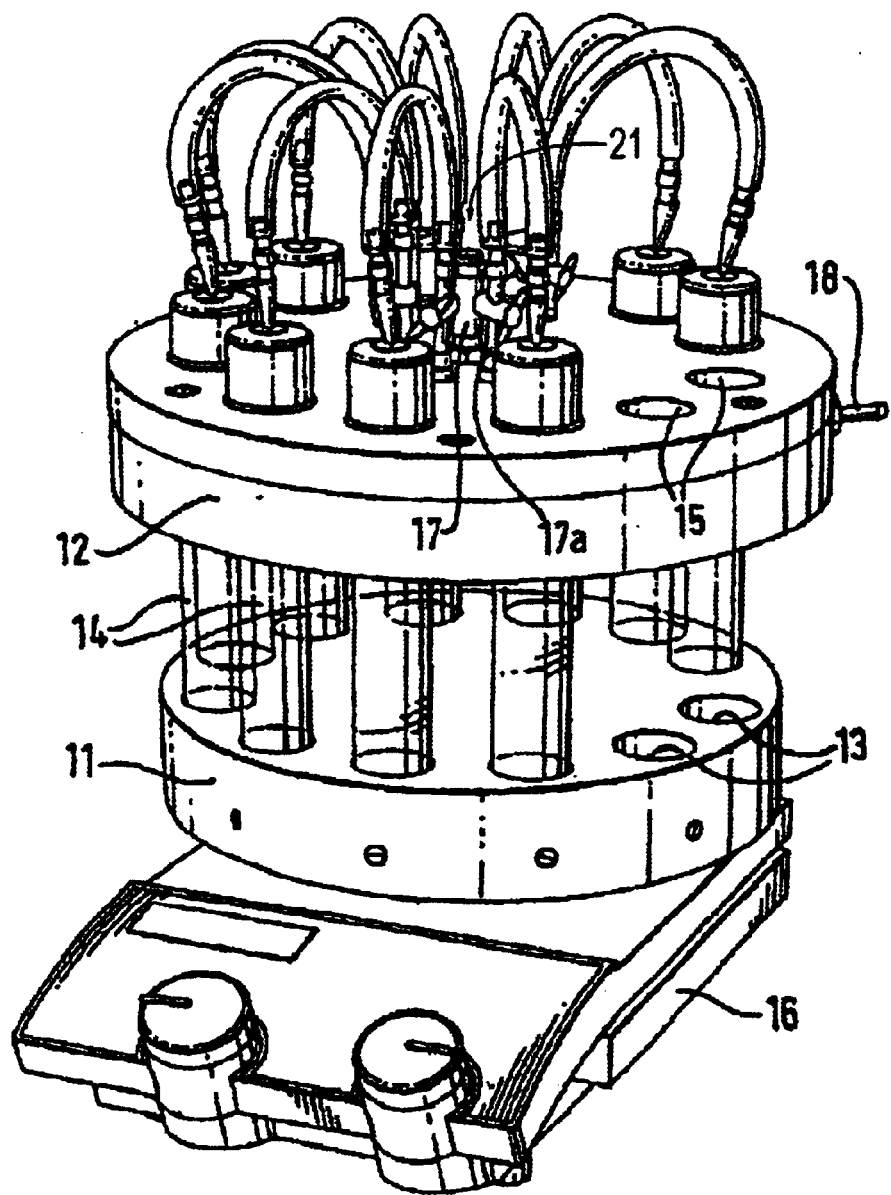
FIG. 4 is a perspective view of the adapter block together with a condenser unit working in co-operation with a laboratory magnetic stirrer.

The device shown in FIGS. 3 and 4 comprises an adapter block (11) and a condenser unit (12) both of which are constructed from aluminum and are circular in shape. The adapter block comprises fixing means in the form of sockets (13) located about the perimeter of the device suitable for accommodating the test tube reaction vessels (14). The condenser unit contains openings (15) through which the test tube reaction vessels pass. The condenser unit is equipped with inlet/outlets (18) which permit cooling fluid to flow through the condenser unit. The adapter block and condenser unit are substantially parallel to one another. One face of the adapter block is equipped with a recess whereby the hotplate of a hotplate/magnetic stirrer (16) may be secured within the recess thereby ensuring that the adapter block is effectively located within the magnetic field. A gas manifold, shown generally at 21, comprising a gas inlet (17) and gas outlets (17a) is located at the centre of the condenser unit.

Figure 5:
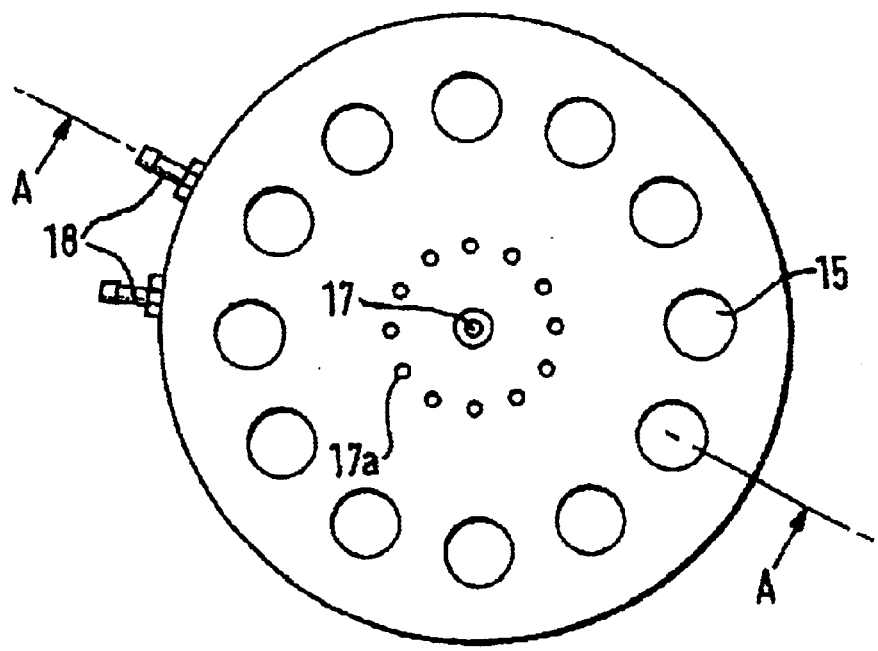
FIG. 5 is a plan view of the condenser unit.
Figure 6:
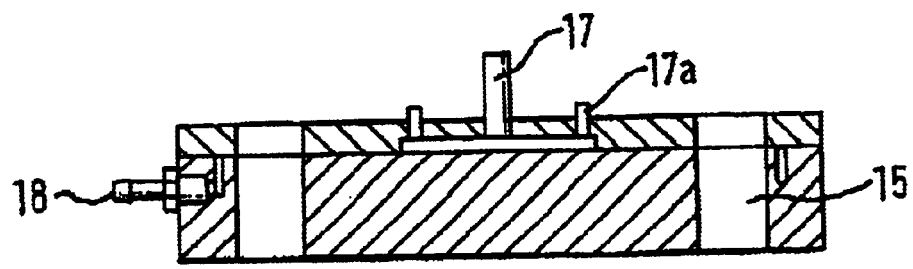
FIG. 6 is a cross-section of the condenser unit along line A.

FIGS. 5 and 6 illustrate more clearly the cooling fluid inlet/outlets (18) the openings through the reaction vessels pass (15) and the gas inlet (17) and the gas outlets (17a).

In an additional embodiment of the invention the device comprises an adapter block as described hereinbefore wherein the device is permanently fixed to a laboratory magnetic or hotplate magnetic stirrer.

What is claimed is:

1. A device comprising an adapter block for seating on a laboratory magnetic stirrer and having a recess in a base thereof for receiving an upper portion of the stirrer, the adapter block containing fixing means for holding a plurality of reaction vessels, wherein when the adapter block is co-operatively positioned on a magnetic stirrer within a magnetic field generated by the magnetic stirrer, each and every position for holding a reaction vessel is effectively located for stirring with respect to the magnetic field, with the center of each vessel distributed around the recess outside the periphery of the recess.

2. The device according to claim 1, wherein the adapter block incorporates guide means to ensure that each and every position for holding a reaction vessel is effectively located for equivalent stirring.

3. The device according to claim 1 wherein the fixing means comprise a plurality of sockets each designed to securely accommodate a reaction vessel.

4. The device according to claim 3 wherein the sockets are arranged about the perimeter of the adapter block.

5. The device according to claim 1 further comprising a condenser unit operatively connected to the adapter block.

6. The device according to claim 5 wherein the adapter block is made of heat conducting material.

7. The device according to claim 1 wherein the adapter block is circular in shape.

8. The device according to claim 1 wherein the adapter block is made of chemically resistant material.

9. The device according to claim 1 further comprising a gas manifold operatively connected to the adapter block.

10. The device according to claim 1, wherein the fixing means comprises a plurality of holders.

11. The device according to claim 1, wherein a base portion of each vessel may be held substantially at the level of the recess.

12. A magnetic stirrer comprising an adapter block wherein the adapter block includes a recess in a base thereof for receiving an upper portion of the stirrer in which a magnetic field is generated, and includes fixing means comprising a plurality of sockets for holding a plurality of reaction vessels with their centers distributed around the recess outside the periphery of the recess, and wherein the adapter block is positioned within the magnetic field generated by the magnetic stirrer such that each and every socket is effectively positioned for stirring with respect to the magnetic field.

13. The magnetic stirrer according to claim 12 further comprising a hotplate operatively connected to the magnetic stirrer and a condenser unit operatively connected to the adapter block.

14. The magnetic stirrer according to claim 12, wherein the fixing means comprises a plurality of holders.

15. The device according to claim 12, wherein a base portion of each vessel may be held substantially at the level of the recess.

16. A magnetic stirrer comprising an adapter block wherein the adapter block contains fixing means comprising a plurality of sockets for holding a plurality of reaction vessels, the adapter block positioned within the magnetic field generated by the magnetic stirrer such that each and every socket of the fixing means is effectively positioned for stirring with respect to a magnetic field generated by the magnetic stirrer, and further comprising a condenser unit operatively connected to the adapter block.

17. The device according to claim 16, wherein the adapter block includes a recess in a base thereof for receiving an upper portion of the stirrer.

18. The device according to claim 17, wherein the centers of the reaction vessels are distributed around the recess outside the periphery of the recess.

19. The device according to claim 18, wherein a base portion of each vessel may be held substantially at the level of the recess.

* * * * *